US012608859B2

(12) United States Patent
Hamaguchi et al.

(10) Patent No.: US 12,608,859 B2
(45) Date of Patent: Apr. 21, 2026

(54) MOVING IMAGE PROCESSING APPARATUS, MOVING IMAGE PROCESSING METHOD AND PROGRAM, AND MOVING IMAGE DISPLAY SYSTEM FOR DISPLAYING INFORMATION RELATED TO AN OBJECT IN THE MOVING IMAGE

(71) Applicant: FUJIFILM Corporation, Tokyo (JP)

(72) Inventors: Yuya Hamaguchi, Kanagawa (JP); Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 50 days.

(21) Appl. No.: 18/495,790

(22) Filed: Oct. 27, 2023

(65) Prior Publication Data

US 2024/0054707 A1 Feb. 15, 2024

Related U.S. Application Data

(63) Continuation of application No. PCT/JP2022/014346, filed on Mar. 25, 2022.

(30) Foreign Application Priority Data

May 6, 2021 (JP) ................................ 2021-078435

(51) Int. Cl.
*G06T 11/00* (2006.01)
*A61B 8/00* (2006.01)
(Continued)

(52) U.S. Cl.
CPC .............. *G06T 11/60* (2013.01); *A61B 8/463* (2013.01); *G06T 7/70* (2017.01); *G06V 10/764* (2022.01);
(Continued)

(58) Field of Classification Search
CPC . G06T 11/60; G06T 7/70; G06T 2207/10016; G06T 2207/10068; G16H 30/40; A61B 8/463; G06V 2201/031
See application file for complete search history.

(56) References Cited

U.S. PATENT DOCUMENTS

2017/0258295 A1* 9/2017 Kronman ......... A61B 1/000094
2018/0210080 A1* 7/2018 Misono ................ A61B 8/4483
(Continued)

FOREIGN PATENT DOCUMENTS

JP 2020175051 10/2020
JP 2020175051 A * 10/2020
(Continued)

OTHER PUBLICATIONS

"International Search Report (Form PCT/ISA/210) of PCT/JP2022/014346", mailed on Jun. 14, 2022, with English translation thereof, pp. 1-5.
(Continued)

*Primary Examiner* — Terrell M Robinson
(74) *Attorney, Agent, or Firm* — JCIPRNET

(57) ABSTRACT

The present disclosure allows information on an object included in a moving image to be superimposed on the moving image and displayed with high visibility. Position information and type information of an object included in frame images of an acquired moving image are acquired, a first display position at which the position information is to be displayed and a second display position at which the type information is to be displayed are determined, the sequentially acquired frame images are sequentially displayed on a display, the position information and the type information are displayed so as to be superimposed on each of the displayed frame images at the first display position and the second display position, the first display position is updated with a first update frequency, and the second display position
(Continued)

is updated with a second update frequency lower than the first update frequency.

14 Claims, 8 Drawing Sheets

(51) Int. Cl.

| | |
|---|---|
| *G06T 7/70* | (2017.01) |
| *G06T 11/60* | (2006.01) |
| *G06V 10/764* | (2022.01) |
| *G06V 20/50* | (2022.01) |
| *G06V 20/70* | (2022.01) |
| *G16H 30/40* | (2018.01) |

(52) U.S. Cl.
CPC .............. *G06V 20/50* (2022.01); *G06V 20/70* (2022.01); *G16H 30/40* (2018.01); *G06T 2207/10016* (2013.01); *G06T 2207/10068* (2013.01); *G06T 2207/10132* (2013.01); *G06T 2207/30004* (2013.01); *G06V 2201/031* (2022.01)

(56) References Cited

U.S. PATENT DOCUMENTS

| | | | | |
|---|---|---|---|---|
| 2018/0310809 | A1* | 11/2018 | Watanabe | .......... A61B 1/00048 |
| 2020/0054399 | A1* | 2/2020 | Duindam | ............... A61B 34/37 |
| 2021/0106209 | A1 | 4/2021 | Usuda | |
| 2021/0174557 | A1* | 6/2021 | Kamon | .............. A61B 1/00147 |
| 2023/0394780 | A1* | 12/2023 | Kamon | ............... G06V 10/273 |

FOREIGN PATENT DOCUMENTS

| | | |
|---|---|---|
| WO | 2017104192 | 6/2017 |
| WO | 2020017212 | 1/2020 |

OTHER PUBLICATIONS

"Written Opinion of the International Searching Authority (Form PCT/ISA/237) of PCT/JP2022/014346", mailed on Jun. 14, 2022, with English translation thereof, pp. 1-11.
"Notice of Reasons for Refusal of Japan Counterpart Application", issued on Feb. 12, 2026, with English translation thereof, p. 1-p. 2.

* cited by examiner

2

10

24

42
38
36

22

44

62
64
50
52
20a
54

20

28

30

32

14  ENDOSCOPE PROCESSOR DEVICE

LIGHT SOURCE DEVICE  16

WATER SUPPLY TANK  70

26

34

18

MONITOR

SUCTION PUMP  72

ULTRASONIC PROCESSOR DEVICE

12

MOVING IMAGE PROCESSING APPARATUS, MOVING IMAGE PROCESSING METHOD AND PROGRAM, AND MOVING IMAGE DISPLAY SYSTEM FOR DISPLAYING INFORMATION RELATED TO AN OBJECT IN THE MOVING IMAGE

CROSS-REFERENCE TO RELATED APPLICATIONS

The present application is a Continuation of PCT International Application No. PCT/JP2022/014346 filed on Mar. 25, 2022 claiming priority under 35 U.S.C § 119(a) to Japanese Patent Application No. 2021-078435 filed on May 6, 2021. Each of the above applications is hereby expressly incorporated by reference, in its entirety, into the present application.

BACKGROUND OF THE INVENTION

1. Field of the Invention

The present invention relates to a moving image processing apparatus, a moving image processing method and program, and a moving image display system, and more specifically to a technique for displaying information concerning an object in a moving image.

2. Description of the Related Art

Ultrasonic endoscopes are operated such that a desired organ appears on a screen while positional relationships between organs and blood vessels are being checked on the screen, but this operation is very difficult. For simplification of such scope operations, it is considered to detect anatomical regions such as an organ and a blood vessel by using image recognition technology such as AI (artificial intelligence) based image recognition and present the anatomical regions to a user. WO2017/104192A discloses a medical observation system that generates candidate lesion moving image data with a combined marker indicating a candidate lesion region detected from a moving image and displays, on a display screen, observation image data based on the candidate lesion moving image data.

SUMMARY OF THE INVENTION

Examples of a display method for presenting an anatomical region to a user include a means for displaying the name of a detected anatomical region in text at the center of the anatomical region. Normally, text is displayed so as to be added to a frame enclosing the anatomical region.

In the detection of an object in a still image, displayed text is fixed, and thus no problem is likely to occur with visibility. In the detection of an object in a moving image, in contrast, if displayed text moves a large amount, the content of the text is difficult to identify at a glance. Thus, there is a problem of poor visibility.

In EUS (Endoscopic ultrasonography), in particular, unlike body surface US (ultrasonography), a user performs a scope operation with their both hands, and an environment that allows switching between display and hiding in response to the user's input is not always provided. Therefore, the display needs to be provided in a manner that does not interfere with the user.

The present invention has been made in view of such circumstances, and an object thereof is to provide a moving image processing apparatus, a moving image processing method and program, and a moving image display system for allowing information on an object included in a moving image to be superimposed on the moving image and displayed with high visibility.

To achieve the object described above, a moving image processing apparatus according to a first aspect includes at least one processor and at least one memory that stores an instruction to be executed by the at least one processor. The at least one processor sequentially acquires frame images of a moving image, acquires position information and type information of an object included in the frame images, the position information indicating a position of the object in the frame images, the type information indicating a type of the object, determines a first display position at which the position information is to be displayed, determines a second display position at which the type information is to be displayed, sequentially displays the sequentially acquired frame images on a display, displays the position information such that the position information is superimposed on each of the displayed frame images at the first display position, displays the type information such that the type information is superimposed on each of the displayed frame images at the second display position, updates the first display position with a first update frequency, and updates the second display position with a second update frequency lower than the first update frequency.

A moving image processing apparatus according to a second aspect of the present invention is the moving image processing apparatus according to the first aspect, in which the first update frequency is every frame image.

A moving image processing apparatus according to a third aspect of the present invention is the moving image processing apparatus according to the first aspect or the second aspect, in which the at least one processor updates the second display position when the first display position at a time when the second display position is last updated is away from the first display position at a current time at a distance greater than or equal to a threshold value.

A moving image processing apparatus according to a fourth aspect of the present invention is the moving image processing apparatus according to any one of the first to third aspects, in which the position information is a bounding box indicating a range of the object.

A moving image processing apparatus according to a fifth aspect of the present invention is the moving image processing apparatus according to the fourth aspect, in which the at least one processor updates the second display position when the bounding box at a time when the second display position is last updated and the bounding box at a current time do not overlap.

A moving image processing apparatus according to a sixth aspect of the present invention is the moving image processing apparatus according to the fourth aspect, in which the at least one processor updates the second display position when an area of an overlapping portion of the bounding box at a time when the second display position is last updated and the bounding box at a current time is less than or equal to a threshold value.

A moving image processing apparatus according to a seventh aspect of the present invention is the moving image processing apparatus according to any one of the first to sixth aspects, in which the at least one processor displays the type information such that the type information is superimposed on only a frame image on which the position information is displayed so as to be superimposed among the frame images.

A moving image processing apparatus according to an eighth aspect of the present invention is the moving image processing apparatus according to any one of the first to seventh aspects, in which the type information includes text information of at least one of a name or an abbreviation of the object.

A moving image processing apparatus according to a ninth aspect of the present invention is the moving image processing apparatus according to any one of the first to eighth aspects, in which the moving image is a medical moving image.

A moving image processing apparatus according to a tenth aspect of the present invention is the moving image processing apparatus according the ninth aspect, in which the medical moving image is an ultrasound moving image.

A moving image processing apparatus according to an eleventh aspect of the present invention is the moving image processing apparatus according to the tenth aspect, in which the ultrasound moving image is captured with an ultrasonic endoscope, and the object includes an organ.

A moving image display system according to a twelfth aspect of the present invention includes an imaging device that captures a moving image, a display, and the moving image processing apparatus according to any one of the first to eleventh aspects.

A moving image processing method according to a thirteenth aspect of the present invention includes a moving image acquisition step of sequentially acquiring frame images of a moving image; an object information acquisition step of acquiring position information and type information of an object included in the frame images, the position information indicating a position of the object in the frame images, the type information indicating a type of the object; a display position determination step of determining a first display position at which the position information is to be displayed and a second display position at which the type information is to be displayed; a display step of sequentially displaying the sequentially acquired frame images on a display, displaying the position information such that the position information is superimposed on each of the displayed frame images at the first display position, and displaying the type information such that the type information is superimposed on each of the displayed frame images at the second display position; and an update step of updating the first display position with a first update frequency and updating the second display position with a second update frequency lower than the first update frequency.

A program according to a fourteenth aspect of the present invention causes a computer to execute the moving image processing method according to the thirteenth aspect. This aspect may also include a non-transitory computer-readable storage medium storing the program.

According to the present invention, information on an object included in a moving image can be superimposed on the moving image and displayed with high visibility.

DESCRIPTION OF THE PREFERRED EMBODIMENTS

Preferred embodiments of the present invention will be described in detail hereinafter with reference to the accompanying drawings.

Existing Display of Moving Image

Figure 1:
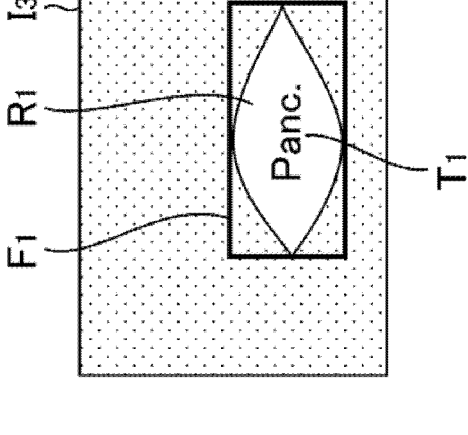
FIG. 1 is a diagram illustrating a moving image displayed by an existing ultrasonic endoscope system.
Figure 1:
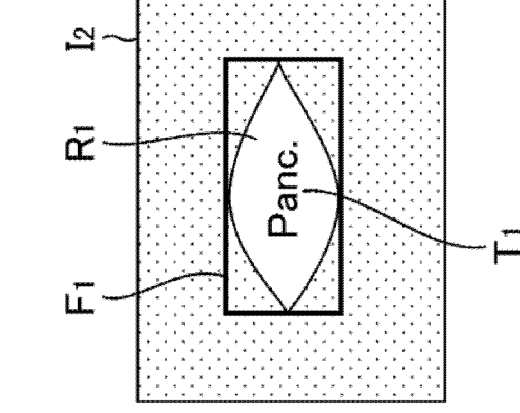
Figure 1:
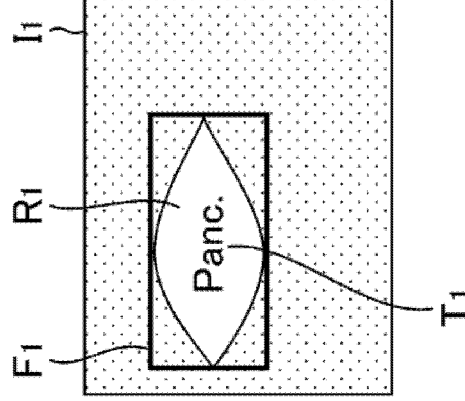

FIG. 1 is a diagram illustrating a moving image displayed by an existing ultrasonic endoscope system. FIG. 1 illustrates an example in which three medical images $I_1$, $I_2$, and $I_3$, which are time-series frame images of the moving image, are sequentially displayed on a monitor.

In each of the medical images $I_1$, $I_2$, and $I_3$, position information $F_1$ indicating the position of a region of interest $R_1$ detected from the medical images $I_1$, $I_2$, and $I_3$ and type information $T_1$ indicating the type of the region of interest $R_1$ are displayed so as to be superimposed on the region of interest $R_1$. In the example illustrated in FIG. 1, the position information $F_1$ is a bounding box indicating the range of the region of interest $R_1$, and the type information $T_1$ is text information indicating the abbreviation of an organ that is the region of interest $R_1$. The position information $F_1$ and the type information $T_1$ are updated every frame. The type information $T_1$ is always displayed at the center of the position information $F_1$.

In the detection of an object in a moving image, as described above, if the type information such as displayed text moves in real time, the visibility becomes poor, and the content of the text is difficult to identify at a glance. In an ultrasonic processor device that functions as a moving image processing apparatus according to the present invention, by contrast, information on a region of interest included in a medical image is superimposed on an ultrasound moving image (an example of a medical moving image) and displayed with high visibility.

Overall Configuration of Ultrasonic Endoscope System

Figure 2:
FIG. 2 is a schematic diagram illustrating an overall configuration of an ultrasonic endoscope system according to the present embodiment.

FIG. 2 is a schematic diagram illustrating an overall configuration of an ultrasonic endoscope system according to the present embodiment. As illustrated in FIG. 2, an ultrasonic endoscope system 2 (an example of a moving image display system) includes an ultrasound scope 10, an ultrasonic processor device 12 that generates an ultrasound image, an endoscope processor device 14 that generates an endoscopic image, a light source device 16 that supplies illumination light to the ultrasound scope 10 to illuminate the inside of a body cavity, and a monitor 18 that displays the ultrasound image and the endoscopic image.

The ultrasound scope 10 (an example of an imaging device) includes an insertion section 20 to be inserted into a body cavity of a subject, a handheld operation section 22 coupled to a proximal end portion of the insertion section 20 and to be operated by an operator, and a universal cord 24 having one end connected to the handheld operation section 22. The other end of the universal cord 24 is provided with an ultrasonic connector 26 to be connected to the ultrasonic processor device 12, an endoscope connector 28 to be connected to the endoscope processor device 14, and a light source connector 30 to be connected to the light source device 16.

The ultrasound scope 10 is detachably connected to the ultrasonic processor device 12, the endoscope processor device 14, and the light source device 16 through the connectors 26, 28, and 30, respectively. The light source connector 30 is also connected to an air/water supply tube 32 and a suction tube 34.

The monitor 18 (an example of a display) receives respective video signals generated by the ultrasonic processor device 12 and the endoscope processor device 14 and displays an ultrasound image and an endoscopic image. The ultrasound image and the endoscopic image can be displayed such that only one of the images is appropriately switched and displayed on the monitor 18 or both of the images are simultaneously displayed.

The handheld operation section 22 is provided with an air/water supply button 36 and a suction button 38, which are arranged side by side, and is also provided with a pair of angle knobs 42 and a treatment tool insertion port 44.

The insertion section 20 has a distal end, a proximal end, and a longitudinal axis 20a. The insertion section 20 is constituted by a tip main body 50, a bending part 52, and an elongated long flexible soft part 54 in this order from the distal end side of the insertion section 20. The tip main body 50 is formed by a hard member. The bending part 52 is coupled to the proximal end side of the tip main body 50. The soft part 54 couples the proximal end side of the bending part 52 to the distal end side of the handheld operation section 22. That is, the tip main body 50 is disposed on the distal end side of the insertion section 20 in the direction of the longitudinal axis 20a. The bending part 52 is remotely operated to bend by turning the pair of angle knobs 42 disposed in the handheld operation section 22. As a result, the tip main body 50 can be directed in a desired direction.

The tip main body 50 is attached with an ultrasound probe 62 and a bag-like balloon 64 that covers the ultrasound probe 62. The balloon 64 can expand or contract when water is supplied from a water supply tank 70 or the water in the balloon 64 is sucked by a suction pump 72. The balloon 64 is inflated until the balloon 64 abuts against the inner wall of the body cavity to prevent attenuation of an ultrasound wave and an ultrasound echo (echo signal) during ultrasound observation.

The tip main body 50 is also attached with an endoscopic observation portion (not illustrated) having an illumination portion and an observation portion including an objective lens, an imaging element, and so on. The endoscopic observation portion is disposed behind the ultrasound probe 62 (on the handheld operation section 22 side).

Moving Image Processing Apparatus

Figure 3:
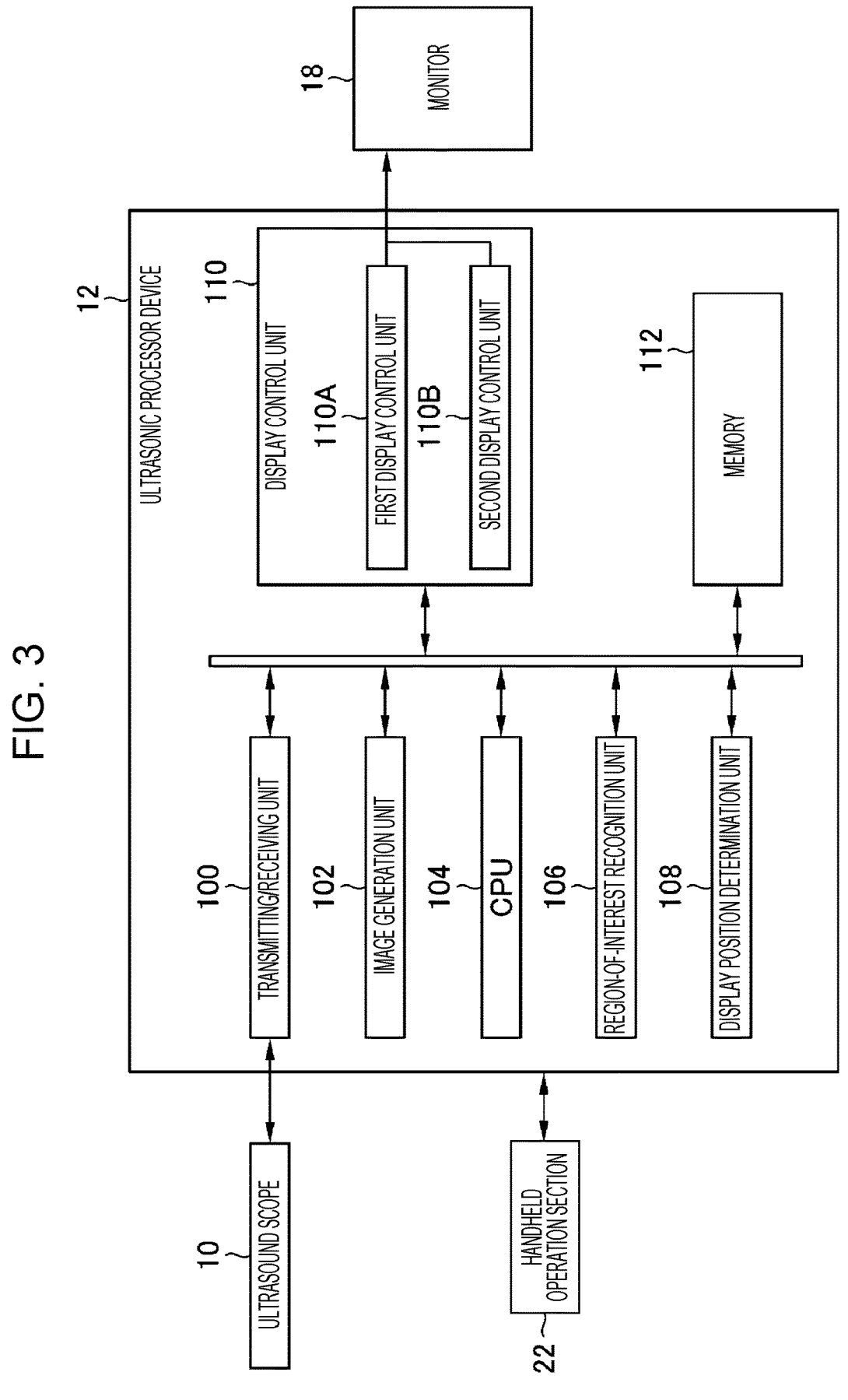
FIG. 3 is a block diagram illustrating an embodiment of an ultrasonic processor device.

FIG. 3 is a block diagram illustrating an embodiment of an ultrasonic processor device that functions as a moving image processing apparatus according to the present invention. The ultrasonic processor device 12 illustrated in FIG. 3 is configured to detect, based on sequentially acquired frame images of an ultrasound moving image, a region of interest in the frame images and notify a user of information indicating a detection result of the region of interest, with the information superimposed on the ultrasound moving image.

As illustrated in FIG. 3, the ultrasonic processor device 12 includes a transmitting/receiving unit 100, an image generation unit 102, a CPU (Central Processing Unit) 104, a region-of-interest recognition unit 106, a display position determination unit 108, a display control unit 110, and a memory 112.

The processes of the transmitting/receiving unit 100, the image generation unit 102, the CPU (Central Processing Unit) 104, the region-of-interest recognition unit 106, the display position determination unit 108, and the display control unit 110 are implemented by at least one processor.

The hardware structure of the processor is implemented as the following various processors. The various processors include a CPU (Central Processing Unit) that is a general-purpose processor executing software (program) to function as various functional units, a GPU (Graphics Processing Unit) that is a processor specialized for image processing, a PLD (Programmable Logic Device) that is a processor whose circuit configuration can be changed after manufacturing, such as an FPGA (Field Programmable Gate Array), a dedicated electric circuit that is a processor having a circuit configuration designed specifically for executing specific processing, such as an ASIC (Application Specific Integrated Circuit), and so on.

A single functional unit may be configured as one of the various processors or as a combination of two or more processors of the same type or different types (such as a plurality of FPGAs, a combination of a CPU and an FPGA, or a combination of a CPU and a GPU, for example). Alternatively, a plurality of functional units may be configured by a single processor. Examples of configuring a plurality of functional units by a single processor include, first, a form in which, as typified by a computer such as a client or server computer, the single processor is configured by a combination of one or more CPUs and software and the processor functions as the plurality of functional units. The examples include, second, a form in which, as typified by a system on chip (SoC) or the like, a processor is used in which the functions of the entire system including the plurality of functional units are implemented as one integrated circuit (IC) chip. As described above, the various functional units are configured using one or more of the various processors described above as a hardware structure.

More specifically, the hardware structure of the various processors is an electric circuit (circuitry) including a combination of circuit elements such as semiconductor elements.

The CPU 104 operates in accordance with various programs stored in the memory 112 and including a moving image processing program according to the present invention to perform overall control of the transmitting/receiving unit 100, the image generation unit 102, the region-of-interest recognition unit 106, the display position determination unit 108, and the display control unit 110, and functions as some of these units.

The transmitting/receiving unit 100 and the image generation unit 102, which function as an ultrasound moving image acquisition processing unit, sequentially acquire time-series frame images of an ultrasound moving image.

A transmitting unit of the transmitting/receiving unit 100 generates a plurality of drive signals to be applied to a plurality of ultrasonic transducers of the ultrasound probe 62 of the ultrasound scope 10, assigns respective delay times to the plurality of drive signals on the basis of a transmission delay pattern selected by a scan control unit (not illustrated), and applies the plurality of drive signals to the plurality of ultrasonic transducers.

A receiving unit of the transmitting/receiving unit 100 amplifies a plurality of detection signals, each of which is output from one of the plurality of ultrasonic transducers of the ultrasound probe 62, and converts the detection signals from analog detection signals to digital detection signals (also referred to as RF (Radio Frequency) data). The RF data is input to the image generation unit 102.

The image generation unit 102 assigns respective delay times to the plurality of detection signals represented by the RF data on the basis of a reception delay pattern selected by the scan control unit and adds the detection signals together to perform reception focus processing. Through the reception focus processing, sound ray data in which the focus of the ultrasound echo is narrowed is formed.

The image generation unit 102 further corrects the sound ray data for attenuation caused by the distance in accordance with the depth of the reflection position of the ultrasound wave by using STC (Sensitivity Time Control), and then performs envelope detection processing on the corrected sound ray data by using a low pass filter or the like to generate envelope data. The image generation unit 102 stores envelope data for one frame or more preferably for a plurality of frames in a cine memory (not illustrated). The image generation unit 102 performs pre-process processing, such as Log (logarithmic) compression or gain adjustment, on the envelope data stored in the cine memory to generate a B-mode image.

In this way, the transmitting/receiving unit 100 and the image generation unit 102 sequentially acquire time-series B-mode images (hereafter referred to as "medical images").

The region-of-interest recognition unit 106 is configured to recognize (detect) a region of interest (an example of an object) included in an input medical image and acquire position information indicating the position of the region of interest in the medical image and type information indicating the type of the region of interest. The region-of-interest recognition unit 106 may be implemented by applying AI (Artificial Intelligence), for example.

In this example, the region of interest is any organ in medical images (tomographic images of B-mode images), and examples of such an organ include the pancreas, the main pancreatic duct, the spleen, the splenic vein, the splenic artery, and the gallbladder.

The position information is, for example, a bounding box indicating the range of the region of interest. The position information is not limited to a bounding box, and may be in a form in which the region of interest is enclosed in a non-rectangular shape such as an elliptical shape, or may be in a form in which the region of interest is filled with a color.

The type information is, for example, text information of at least one of the name or abbreviation of the organ serving as the region of interest. The type information only needs to allow the user to identify the organ serving as the region of interest, and may be a symbol, a figure, a color, or a combination thereof.

The display position determination unit 108 determines a first display position at which the position information of the region of interest is to be displayed and superimposed on the medical image displayed on the monitor 18. The display position determination unit 108 further determines a second display position at which the type information of the region of interest is to be displayed and superimposed on the medical image displayed on the monitor 18. The display position determination unit 108 updates, for the sequentially acquired medical images, the first display position with a first update frequency and the second display position with a second update frequency lower than the first update frequency.

The display control unit 110 includes a first display control unit 110A that causes the monitor 18, which is a display unit, to display an ultrasound moving image, and a second display control unit 110B that causes the monitor 18 to display information related to the region of interest.

The first display control unit 110A causes the monitor 18 to sequentially display the medical images sequentially acquired by the transmitting/receiving unit 100 and the image generation unit 102. In this example, a moving image indicating an ultrasound tomographic image is displayed on the monitor 18.

The second display control unit 110B causes the position information of the region of interest to be displayed and superimposed on the medical image displayed on the monitor 18 by the first display control unit 110A at the first display position determined by the display position determination unit 108 and causes the type information of the region of interest to be displayed and superimposed on the medical image displayed on the monitor 18 by the first display control unit 110A at the second display position determined by the display position determination unit 108.

The memory 112 is at least one memory that stores instructions to be executed by the processor. The memory 112 stores instructions to be executed by the processor. The memory 112 includes a RAM (Random Access Memory) and a ROM (Read Only Memory), which are not illustrated. The processor executes software by using the RAM as a work area and using various programs including a moving image processing program stored in the ROM, and executes various processes of the ultrasonic processor device 12 by using parameters stored in the ROM or the like.

Moving Image Processing Method

Figure 4:
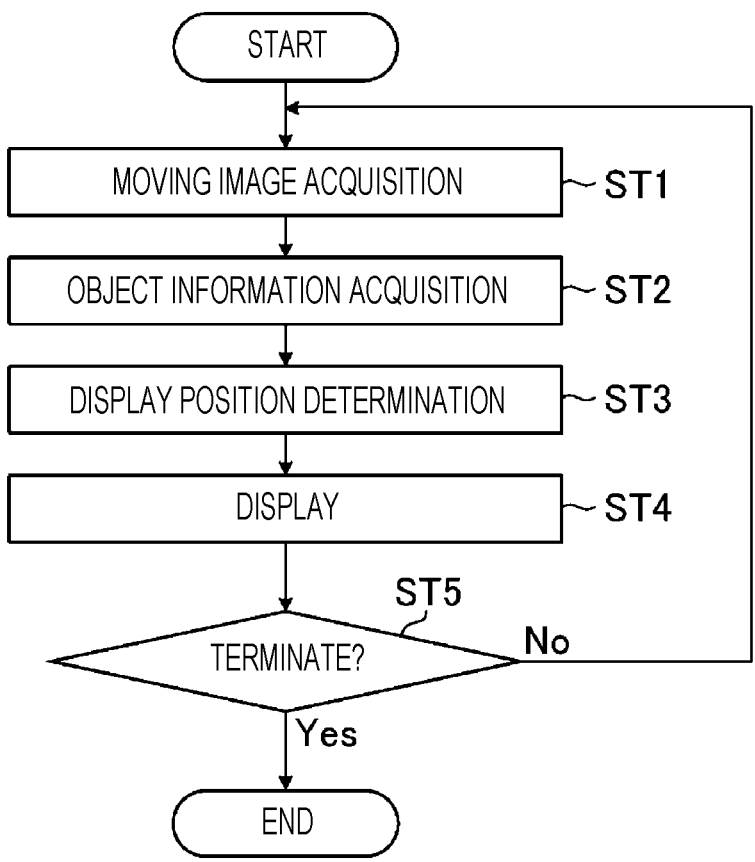
FIG. 4 is a flowchart illustrating steps of a moving image processing method according to the present embodiment.

FIG. 4 is a flowchart illustrating steps of a moving image processing method according to the present embodiment. The moving image processing method is implemented by the CPU 104 executing a moving image processing program stored in the memory 112. The moving image processing program may be provided by a non-transitory storage medium readable by a computer. In this case, the ultrasonic processor device 12 may read the moving image processing program from the non-transitory storage medium and store the moving image processing program in the memory 112.

In step ST1 (an example of a moving image acquisition step), the transmitting/receiving unit 100 and the image generation unit 102 sequentially acquire time-series medical images (an example of frame images) of an ultrasound moving image.

In step ST2 (an example of an object information acquisition step), the region-of-interest recognition unit 106 acquires position information indicating the position of a region of interest included in the medical images acquired in step ST1, and type information indicating the type of the region of interest.

In step ST3 (an example of a display position determination step), the display position determination unit 108 determines a first display position at which the position information acquired in step ST2 is to be displayed and a second display position at which the type information acquired in step ST2 is to be displayed.

In step ST4 (an example of a display step), the first display control unit 110A sequentially displays the medical images sequentially acquired in step ST1 on the monitor 18. Further, the second display control unit 110B superimposes the position information acquired in step ST2 and the type information acquired in step ST2 on the medical image displayed on the monitor 18 and displays the position information at the first display position determined in step ST3 and the type information at the second display position determined in step ST3.

Then, in step ST5, the ultrasonic processor device 12 determines whether to terminate the display of the ultrasound moving image. If the display is to be terminated, the ultrasonic processor device 12 ends the process in this flowchart. If the display is not to be terminated, the ultrasonic processor device 12 returns to the processing of step ST1 and repeats similar processing.

Here, in step ST3 (an example of an update step), the display position determination unit 108 updates the first display position with a first update frequency and updates the second display position with a second update frequency lower than the first update frequency. The update frequencies may be controlled in accordance with time or may be controlled in accordance with a location in an image, as described below.

First Embodiment

In a first embodiment, the display position determination unit 108 updates the first display position of the position information with a first update frequency, namely, every frame (an example of every frame image), and updates the second display position of the type information with a second update frequency lower than the first update frequency, namely, every two frames.

Figure 5:
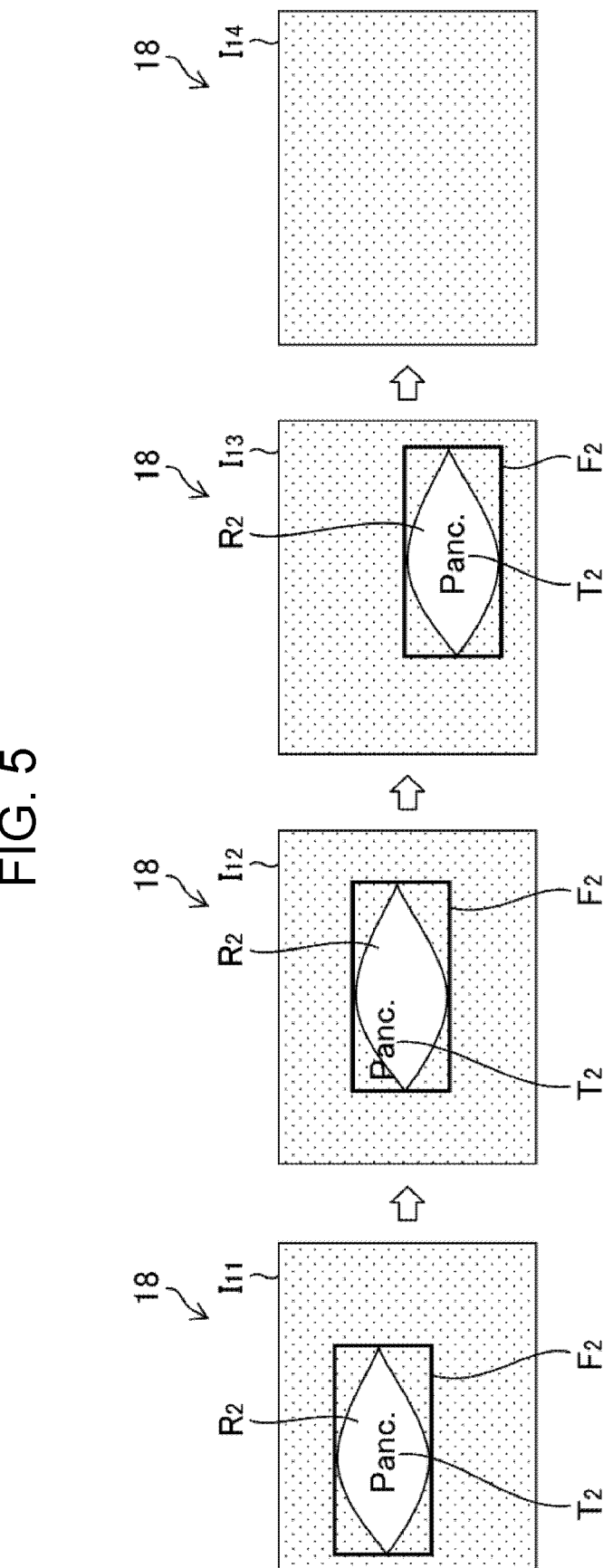
FIG. 5 is a diagram illustrating the display of a moving image according to a first embodiment.

FIG. 5 is a diagram illustrating the display of a moving image according to the first embodiment. FIG. 5 illustrates an example in which four sequentially acquired medical images $I_{11}$, $I_{12}$, $I_{13}$, and $I_{14}$ are sequentially displayed on the monitor 18.

In each of the medical images $I_{11}$, $I_{12}$, and $I_{13}$, which are sequentially displayed on the monitor 18, position information $F_2$ of a detected region of interest $R_2$ and type information $T_2$ of the region of interest $R_2$ are displayed so as to be superimposed on the region of interest $R_2$. The position information $F_2$ is a bounding box indicating the range of the region of interest $R_2$, and the type information $T_2$ is text information indicating the abbreviation of an organ that is the region of interest $R_2$. No region of interest appears in the medical image $I_{14}$.

First, the medical image $I_{11}$ is displayed. The position information $F_2$ of the region of interest $R_2$ and the type information $T_2$ of the region of interest $R_2$ are displayed so as to be superimposed on the medical image $I_{11}$. It is assumed that both the first display position of the position information $F_2$ and the second display position of the type information $T_2$ have been updated at the timing when the medical image $I_{11}$ is displayed. Accordingly, the first display position of the position information $F_2$ and the second display position of the type information $T_2$ on the medical image $I_{11}$ correspond to the position of the region of interest $R_2$ detected in the medical image $I_{11}$. The second display position of the type information $T_2$ is at the center of the position information $F_2$. However, the second display position is not limited to this example and can be determined by the display position determination unit 108, as appropriate.

Then, the medical image $I_{12}$ is displayed. The position information $F_2$ of the region of interest $R_2$ and the type information $T_2$ of the region of interest $R_2$ are displayed so as to be superimposed on the medical image $I_{12}$. Since the first display position of the position information $F_2$ is updated every frame, the position information $F_2$ is displayed so as to be superimposed on the medical image $I_{12}$ at the first display position corresponding to the position of the region of interest $R_2$ detected in the medical image $I_{12}$. Since the second display position of the type information $T_2$ is updated every two frames, the second display position on the medical image $I_{12}$ is the same as the second display position of the type information $T_2$ on the medical image $I_{11}$. Accordingly, the monitor 18 displays the medical image $I_{12}$ with the type information $T_2$ superimposed thereon at the same position as that of the type information $T_2$ on the medical image $I_{11}$.

Then, the medical image $I_{13}$ is displayed. The position information $F_2$ of the region of interest $R_2$ and the type information $T_2$ of the region of interest $R_2$ are displayed so as to be superimposed on the medical image $I_{13}$. Both the first display position of the position information $F_2$ and the second display position of the type information $T_2$ are updated at the timing when the medical image $I_{13}$ is displayed. Accordingly, the first display position of the position information $F_2$ and the second display position of the type information $T_2$ on the medical image $I_{13}$ correspond to the position of the region of interest $R_2$ detected in the medical image $I_{13}$.

Further, the medical image $I_{14}$ is displayed. Since no region of interest is detected from the medical image $I_{14}$, the medical image $I_{14}$ does not display the position information $F_2$ superimposed thereon. Since the second display position of the type information $T_2$ is updated every two frames, the timing at which the medical image $I_{14}$ is displayed does not match the timing at which the second display position of the type information $T_2$ is updated. However, the second display control unit 110B displays the type information $T_2$ such that the type information $T_2$ is superimposed on only a medical image on which the position information $F_2$ is displayed so as to be superimposed. Accordingly, the medical image $I_{14}$ on which the position information $F_2$ is not displayed in a superimposed manner does not also display the type information $T_2$ in a superimposed manner.

As described above, updating the second display position of the type information with a relatively lower update frequency than the first display position of the position information can improve the visibility of the type information, with the position information displayed in accordance with the position of the region of interest.

In addition, the medical image displays the type information in a superimposed manner only when displaying the position information in a superimposed manner, which can prevent unnecessary type information from being displayed in a superimposed manner even when the update frequency of the type information is relatively low.

While the second display position of the type information is updated with a frequency of every two frames, the second display position of the type information may be updated every three or more frames as long as the update frequency is lower than the first update frequency of the display position of the position information.

Second Embodiment

In a second embodiment, the display position determination unit 108 updates the first display position of the position information with the first update frequency, namely, every frame. Further, the display position determination unit 108 updates the second display position when the first display position at the time when the second display position is last updated is away from the first display position at the current time at a distance greater than or equal to a threshold value.

Figure 6:
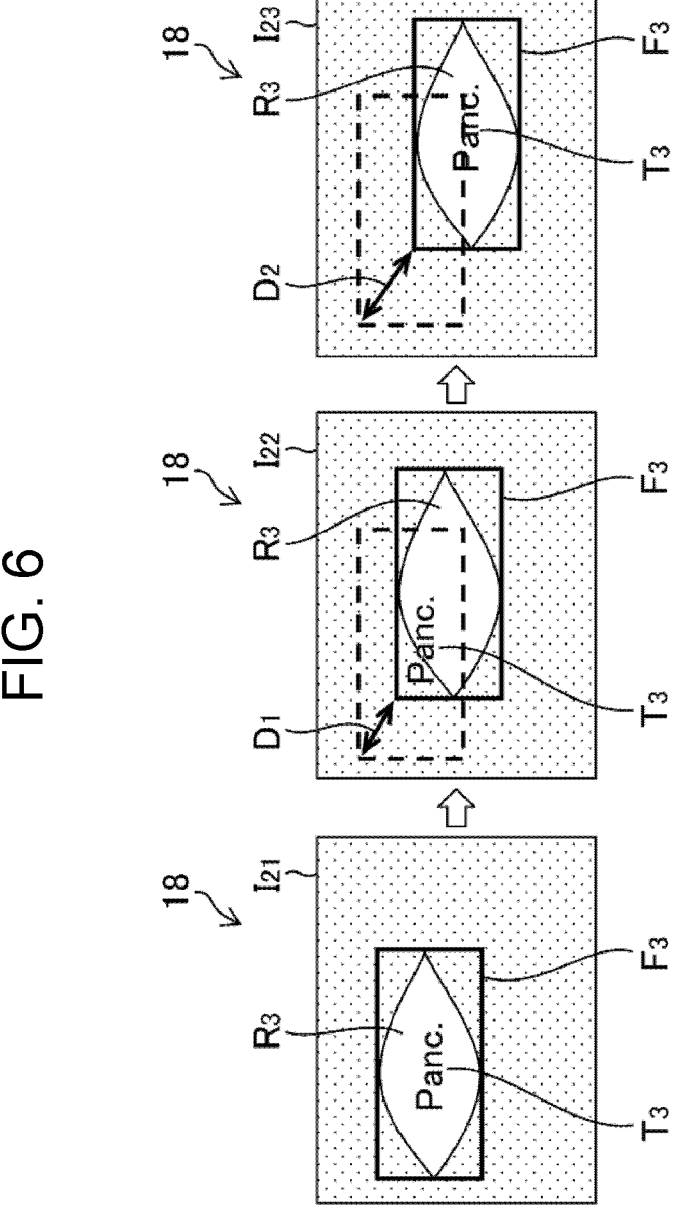
FIG. 6 is a diagram illustrating the display of a moving image according to a second embodiment.

FIG. 6 is a diagram illustrating the display of a moving image according to the second embodiment. FIG. 6 illustrates an example in which three sequentially acquired medical images $I_{21}$, $I_{22}$, and $I_{23}$ are sequentially displayed on the monitor 18.

In each of the medical images $I_{21}$, $I_{22}$, and $I_{23}$, which are sequentially displayed on the monitor 18, position information $F_3$ of a detected region of interest $R_3$ and type information $T_3$ of the region of interest $R_3$ are displayed so as to be superimposed on the region of interest $R_3$. Frames indicated by broken lines in the medical images $I_{22}$ and $I_{23}$ in FIG. 6 represent the display position of the position information $F_3$ on the medical image $I_{21}$ and are illustrated for description. These frames are not displayed on the monitor 18.

First, the medical image $I_{21}$ is displayed. The position information $F_3$ of the region of interest $R_3$ and the type information $T_3$ of the region of interest $R_3$ are displayed so as to be superimposed on the medical image $I_{21}$. It is assumed that both the first display position of the position information $F_3$ and the second display position of the type information $T_3$ have been updated at the timing when the medical image $I_{21}$ is displayed. Accordingly, the first display position of the position information $F_3$ and the second display position of the type information $T_3$ on the medical image $I_{21}$ correspond to the position of the region of interest $R_3$ detected in the medical image $I_{21}$.

Then, the medical image $I_{22}$ is displayed. The position information $F_3$ of the region of interest $R_3$ and the type information $T_3$ of the region of interest $R_3$ are displayed so as to be superimposed on the medical image $I_{22}$. Since the first display position of the position information $F_3$ is updated every frame, the position information $F_3$ is displayed so as to be superimposed on the medical image $I_{22}$ at the first display position corresponding to the position of the region of interest $R_3$ detected in the medical image $I_{22}$.

As used here, the "first display position at the time when the second display position is last updated", which is a reference display position serving as a reference for updating the type information $T_3$, at the time point when the medical image $I_{22}$ is displayed corresponds to the first display position of the position information $F_3$ displayed so as to be superimposed on the medical image $I_{21}$. As illustrated in FIG. 6, a distance between the first display position of the position information $F_3$ displayed so as to be superimposed on the medical image $I_{21}$ and the first display position of the position information $F_3$ displayed so as to be superimposed on the medical image $I_{22}$ is $D_1$. The distance $D_1$ has a relationship of $D_{TH} > D_1$, where $D_{TH}$ is a threshold value stored in the memory 112, and the second display position of the type information $T_3$ on the medical image $I_{22}$ is not updated. Accordingly, the type information $T_3$ is displayed so as to be superimposed on the medical image $I_{22}$ at the same position as that of the type information $T_3$ on the medical image $I_{21}$.

The threshold value $D_{TH}$ need not be a fixed value and may be changed in accordance with the size of the detected region of interest (the size of the bounding box) in the image.

Then, the medical image $I_{23}$ is displayed. The position information $F_3$ of the region of interest $R_3$ and the type information $T_3$ of the region of interest $R_3$ are displayed so as to be superimposed on the medical image $I_{23}$. Since the first display position of the position information $F_3$ is updated every frame, the position information $F_3$ is displayed so as to be superimposed on the medical image $I_{23}$ at the first display position corresponding to the position of the region of interest $R_3$ detected in the medical image $I_{23}$.

The reference display position at the time point when the medical image $I_{23}$ is displayed also corresponds to the first display position of the position information $F_3$ displayed so as to be superimposed on the medical image $I_{21}$. As illustrated in FIG. 6, a distance between the first display position of the position information $F_3$ displayed so as to be superimposed on the medical image $I_{21}$ and the first display position of the position information $F_3$ displayed so as to be superimposed on the medical image $I_{23}$ is $D_2$. Since the distance $D_2$ and the threshold value $D_{TH}$ have a relationship of $D_{TH} \leq D_2$, the second display position of the type information $T_3$ on the medical image $I_{23}$ is updated. In the medical image $I_{23}$, accordingly, the type information $T_3$ is displayed at the center of the position information $F_3$. In the subsequent medical images, the reference display position is the first display position of the position information $F_3$ displayed so as to be superimposed on the medical image $I_{23}$.

As described above, according to the second embodiment, it is possible to improve the visibility of the type information, with the position information displayed in accordance with the position of the region of interest.

Third Embodiment

In a third embodiment, the display position determination unit 108 updates the first display position of the position information with the first update frequency, namely, every frame. Further, the display position determination unit 108 updates the second display position when the bounding box at the time when the second display position is last updated and the bounding box at the current time do not overlap.

Figure 7:
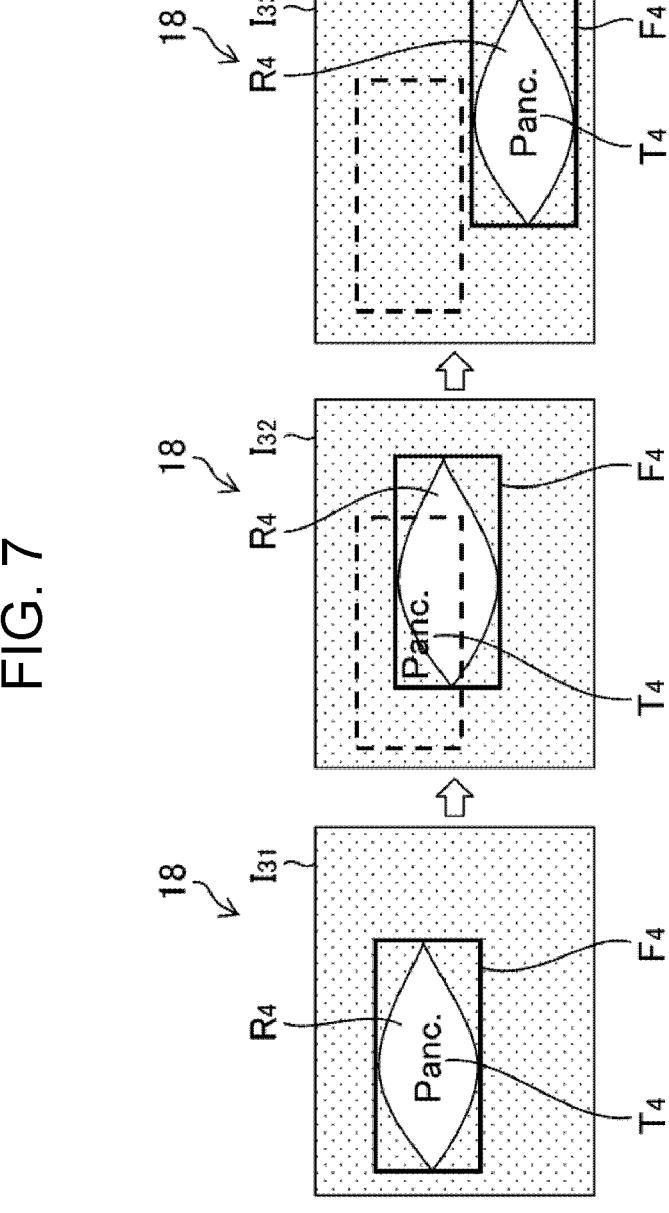
FIG. 7 is a diagram illustrating the display of a moving image according to a third embodiment.

FIG. 7 is a diagram illustrating the display of a moving image according to the third embodiment. FIG. 7 illustrates an example in which three sequentially acquired medical images $I_{31}$, $I_{32}$, and $I_{33}$ are sequentially displayed on the monitor 18.

In each of the medical images $I_{31}$, $I_{32}$, and $I_{33}$, which are sequentially displayed on the monitor 18, position information $F_4$ of a detected region of interest $R_4$ and type information $T_4$ of the region of interest $R_4$ are displayed so as to be superimposed on the region of interest $R_4$. Frames indicated by broken lines in the medical images $I_{32}$ and $I_{33}$ represent the display position of the position information $F_4$ on the medical image $I_{31}$ and are illustrated for description. These frames are not displayed on the monitor 18.

First, the medical image $I_{31}$ is displayed. The position information $F_4$ of the region of interest $R_4$ and the type information $T_4$ of the region of interest $R_4$ are displayed so as to be superimposed on the medical image $I_{31}$. It is assumed that both the first display position of the position information $F_4$ and the second display position of the type information $T_4$ have been updated at the timing when the medical image $I_{31}$ is displayed. Accordingly, the first display position of the position information $F_4$ and the second display position of the type information $T_4$ on the medical image $I_{31}$ correspond to the position of the region of interest $R_4$ detected in the medical image $I_{31}$.

Then, the medical image $I_{32}$ is displayed. The position information $F_4$ of the region of interest $R_4$ and the type information $T_4$ of the region of interest $R_4$ are displayed so as to be superimposed on the medical image $I_{32}$. Since the first display position of the position information $F_4$ is updated every frame, the position information $F_4$ is displayed so as to be superimposed on the medical image $I_{32}$ at the first display position corresponding to the position of the region of interest $R_4$ detected in the medical image $I_{32}$.

The "bounding box at the time when the second display position is last updated", which is a reference bounding box serving as a reference for updating the type information $T_4$, at the time point when the medical image $I_{32}$ is displayed corresponds to the bounding box of the position information $F_4$ displayed so as to be superimposed on the medical image $I_{31}$. As illustrated in FIG. 7, the bounding box of the position information $F_4$ displayed so as to be superimposed on the medical image $I_{31}$ and the bounding box of the position information $F_4$ displayed so as to be superimposed on the medical image $I_{32}$ partially overlap. Accordingly, the second display position of the type information $T_4$ on the medical image $I_{32}$ is not updated, and the type information $T_4$ is displayed so as to be superimposed on the medical image $I_{32}$ at the same position as that of the type information $T_4$ on the medical image $I_{31}$.

Then, the medical image $I_{33}$ is displayed. The position information $F_4$ of the region of interest $R_4$ and the type information $T_4$ of the region of interest $R_4$ are displayed so as to be superimposed on the medical image $I_{33}$. Since the first display position of the position information $F_4$ is updated every frame, the position information $F_4$ is displayed so as to be superimposed on the medical image $I_{33}$ at the first display position corresponding to the position of the region of interest $R_4$ detected in the medical image $I_{33}$.

The reference bounding box at the time point when the medical image $I_{33}$ is displayed corresponds to the bounding box of the position information $F_4$ displayed so as to be superimposed on the medical image $I_{31}$. As illustrated in FIG. 7, the bounding box of the position information $F_4$ displayed so as to be superimposed on the medical image $I_{31}$ and the bounding box of the position information $F_4$ displayed so as to be superimposed on the medical image $I_{33}$ do not overlap. Accordingly, the second display position of the type information $T_4$ on the medical image $I_{33}$ is updated, and the type information $T_4$ on the medical image $I_{33}$ is displayed at the center of the position information $F_4$. In the subsequent medical images, the reference bounding box is the bounding box of the position information $F_4$ displayed so as to be superimposed on the medical image $I_{33}$.

As described above, according to the third embodiment, it is possible to improve the visibility of the type information, with the position information displayed in accordance with the position of the region of interest.

Fourth Embodiment

In a fourth embodiment, the display position determination unit 108 updates the first display position of the position information with the first update frequency, namely, every frame. Further, the display position determination unit 108 updates the second display position when the area of an overlapping portion of the bounding box at the time when the second display position is last updated and the bounding box at the current time is less than or equal to a threshold value.

Figure 8:
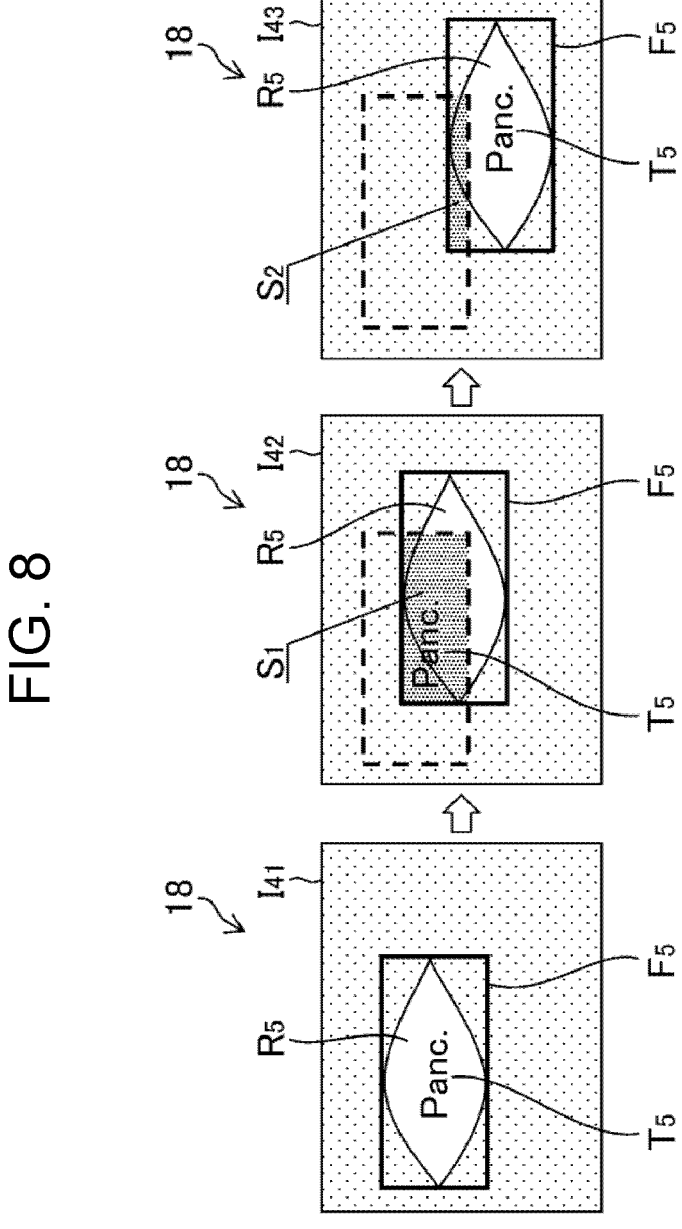
FIG. 8 is a diagram illustrating the display of a moving image according to a fourth embodiment.

FIG. 8 is a diagram illustrating the display of a moving image according to the fourth embodiment. FIG. 8 illustrates an example in which three sequentially acquired medical images $I_{41}$, $I_{42}$, and $I_{43}$ are sequentially displayed on the monitor 18.

In each of the medical images $I_{41}$, $I_{42}$, and $I_{43}$, which are sequentially displayed on the monitor 18, position information $F_5$ of a detected region of interest $R_5$ and type information $T_5$ of the region of interest $R_5$ are displayed so as to be superimposed on the region of interest $R_5$. Frames indicated by broken lines in the medical images $I_{42}$ and $I_{43}$ represent the display position of the position information $F_5$ on the medical image $I_{41}$ and are illustrated for description. These frames are not displayed on the monitor 18.

First, the medical image $I_{41}$ is displayed. The position information $F_5$ of the region of interest $R_5$ and the type information $T_5$ of the region of interest $R_5$ are displayed so as to be superimposed on the medical image $I_{41}$. It is assumed that both the first display position of the position information $F_5$ and the second display position of the type information $T_5$ have been updated at the timing when the medical image $I_{41}$ is displayed. Accordingly, the first display position of the position information $F_5$ and the second display position of the type information $T_5$ on the medical image $I_{41}$ correspond to the position of the region of interest $R_5$ detected in the medical image $I_{41}$.

Then, the medical image $I_{42}$ is displayed. The position information $F_5$ of the region of interest $R_5$ and the type information $T_5$ of the region of interest $R_5$ are displayed so as to be superimposed on the medical image $I_{42}$. Since the first display position of the position information $F_5$ is updated every frame, the position information $F_5$ is displayed so as to be superimposed on the medical image $I_{42}$ at the first display position corresponding to the position of the region of interest $R_5$ detected in the medical image $I_{42}$.

The "bounding box at the time when the second display position is last updated", which is a reference bounding box serving as a reference for updating the type information $T_5$, at the time point when the medical image $I_{42}$ is displayed corresponds to the bounding box of the position information $F_5$ displayed so as to be superimposed on the medical image $I_{41}$, as in the third embodiment. As illustrated in FIG. 8, the bounding box of the position information $F_5$ displayed so as to be superimposed on the medical image $I_{41}$ and the bounding box of the position information $F_5$ displayed so as to be superimposed on the medical image $I_{42}$ partially overlap, and the area of the overlapping portion is $S_1$. The area $S_1$ has a relationship of $S_{TH}<S_1$, where $S_{TH}$ is a threshold value stored in the memory 112, and the second display position of the type information $T_5$ on the medical image $I_{42}$ is not updated. Accordingly, the type information $T_5$ is displayed so as to be superimposed on the medical image $I_{42}$ at the same position as that of the type information $T_5$ on the medical image $I_{41}$.

The "area of the overlapping portion", as considered here, may be an absolute value on an image or a proportion to the area of the bounding box. The threshold value $S_{TH}$ may be changed in accordance with the size of the detected region of interest (the size of the bounding box) in the image.

Then, the medical image $I_{43}$ is displayed. The position information $F_5$ of the region of interest $R_5$ and the type information $T_5$ of the region of interest $R_5$ are displayed so as to be superimposed on the medical image $I_{43}$. Since the first display position of the position information $F_5$ is updated every frame, the position information $F_5$ is displayed so as to be superimposed on the medical image $I_{43}$ at the first display position corresponding to the position of the region of interest $R_5$ detected in the medical image $I_{43}$.

The reference bounding box at the time point when the medical image $I_{43}$ is displayed corresponds to the bounding box of the position information $F_5$ displayed so as to be superimposed on the medical image $I_{41}$. As illustrated in FIG. 8, the bounding box of the position information $F_5$ displayed so as to be superimposed on the medical image $I_{41}$ and the bounding box of the position information $F_5$ displayed so as to be superimposed on the medical image $I_{43}$ partially overlap, and the area of the overlapping portion is $S_2$. Since the area $S_2$ and the threshold value $S_{TH}$ have a relationship of $S_{TH}>S_2$, the second display position of the type information $T_5$ on the medical image $I_{43}$ is updated. In the medical image $I_{43}$, accordingly, the type information $T_5$ is displayed at the center of the position information $F_5$. In the subsequent medical images, the reference bounding box is the bounding box of the position information $F_5$ displayed so as to be superimposed on the medical image $I_{43}$.

As described above, according to the fourth embodiment, it is possible to improve the visibility of the type information, with the position information displayed in accordance with the position of the region of interest.

Others

In all of the first to fourth embodiments, the first display position of the position information is updated every frame. Alternatively, the first update frequency for the first display position of the position information need not be every frame image. For example, the first update frequency may be determined in accordance with the frequency with which the region-of-interest recognition unit 106 acquires position information. For example, when the region-of-interest recognition unit 106 acquires position information in units of a plurality of frames, the first update frequency may be set in accordance with the frequency with which the region-of-interest recognition unit 106 acquires position information.

In the first to fourth embodiments, an ultrasound moving image captured with an ultrasonic endoscope has been described as an example. However, the present invention can also be applied to a medical moving image other than an ultrasound moving image. The present invention can also be applied to a moving image obtained by capturing images of an object.

The technical scope of the present invention is not limited to the scope described in the embodiments described above. The configurations and the like in the embodiments can be combined as appropriate in the embodiments without departing from the gist of the present invention.

REFERENCE SIGNS LIST 2 ultrasonic endoscope system
10 ultrasound scope
12 ultrasonic processor device
14 endoscope processor device
16 light source device
18 monitor
20 insertion section
20*a* longitudinal axis
22 handheld operation section
24 universal cord
26 ultrasonic connector
28 endoscope connector
30 light source connector
32 tube
34 tube
36 air/water supply button
38 suction button
42 angle knob
44 treatment tool insertion port
50 tip main body
52 bending part
54 soft part
62 ultrasound probe
64 balloon
70 water supply tank
72 suction pump
100 transmitting/receiving unit
102 image generation unit
106 region-of-interest recognition unit
108 display position determination unit
110 display control unit
110A first display control unit
110B second display control unit

16

112 memory
$F_1$ to $F_5$ position information
$I_1$ to $I_3$ medical image
$I_{11}$ to $I_{14}$ medical image
$I_{21}$ to $I_{23}$ medical image
$I_{31}$ to $I_{33}$ medical image
$I_{41}$ to $I_{43}$ medical image
$R_1$ to $R_5$ region of interest
ST1 to ST5 step of moving image processing method
$T_1$ to $T_5$ type information

What is claimed is:

1. A moving image processing apparatus comprising:
at least one processor; and
at least one memory that stores an instruction to be executed by the at least one processor, wherein
the at least one processor is configured to:
sequentially acquire frame images of a moving image,
acquire position information and type information of an object included in the frame images, the position information indicating a position of the object in the frame images, the type information indicating a type of the object,
determine a first display position at which the position information is to be displayed,
determine a second display position at which the type information is to be displayed,
sequentially display the sequentially acquired frame images on a display,
display the position information such that the position information is superimposed on each of the displayed frame images at the first display position,
display the type information such that the type information is superimposed on each of the displayed frame images at the second display position,
update the first display position with a first update frequency, and
update the second display position with a second update frequency lower than the first update frequency, wherein the first display position and the second display position are displayed simultaneously on the display.

2. The moving image processing apparatus according to claim 1, wherein
the first update frequency is every frame image.

3. The moving image processing apparatus according to claim 1, wherein
the at least one processor is configured to:
update the second display position when the first display position at a time when the second display position is last updated is away from the first display position at a current time at a distance greater than or equal to a threshold value.

4. The moving image processing apparatus according to claim 1, wherein
the position information is a bounding box indicating a range of the object.

5. The moving image processing apparatus according to claim 4, wherein
the at least one processor is configured to:
update the second display position when the bounding box at a time when the second display position is last updated and the bounding box at a current time do not overlap.

6. The moving image processing apparatus according to claim 4, wherein the at least one processor is configured to:

update the second display position when an area of an overlapping portion of the bounding box at a time when the second display position is last updated and the bounding box at a current time is less than or equal to a threshold value.

7. The moving image processing apparatus according to claim 1, wherein the at least one processor is configured to:

display the type information such that the type information is superimposed on only a frame image on which the position information is displayed so as to be superimposed among the frame images.

8. The moving image processing apparatus according to claim 1, wherein the type information includes text information of at least one of a name or an abbreviation of the object.

9. The moving image processing apparatus according to claim 1, wherein the moving image is a medical moving image.

10. The moving image processing apparatus according to claim 9, wherein the medical moving image is an ultrasound moving image.

11. The moving image processing apparatus according to claim 10, wherein the ultrasound moving image is captured with an ultrasonic endoscope, and the object includes an organ.

12. A moving image display system comprising:

an imaging device that captures a moving image;

a display; and the moving image processing apparatus according to claim 1.

13. A moving image processing method comprising:

a moving image acquisition step of sequentially acquiring frame images of a moving image;

an object information acquisition step of acquiring position information and type information of an object included in the frame images, the position information indicating a position of the object in the frame images, the type information indicating a type of the object;

a display position determination step of determining a first display position at which the position information is to be displayed and a second display position at which the type information is to be displayed;

a display step of sequentially displaying the sequentially acquired frame images on a display, displaying the position information such that the position information is superimposed on each of the displayed frame images at the first display position, and displaying the type information such that the type information is superimposed on each of the displayed frame images at the second display position; and an update step of updating the first display position with a first update frequency and updating the second display position with a second update frequency lower than the first update frequency, wherein the first display position and the second display position are displayed simultaneously on the display.

14. A non-transitory, computer-readable tangible recording medium which records thereon a program for causing, when read by a computer, the computer to execute the moving image processing method according to claim 13.

* * * * *